United States Patent
Greenberg et al.

(10) Patent No.: US 10,406,361 B2
(45) Date of Patent: Sep. 10, 2019

(54) METHOD AND APPARATUS TO PROVIDE SAFETY CHECKS FOR NEURAL STIMULATION

(71) Applicant: Second Sight Medical Products, Inc., Sylmar, CA (US)

(72) Inventors: Robert Jay Greenberg, Los Angeles, CA (US); Kelly Hobart McClure, Simi Valley, CA (US); James S. Little, Arvada, CO (US); Rongqing Dai, Valencia, CA (US); Arup Roy, Valencia, CA (US); Richard Augustin Castro, Santa Monica, CA (US); John Reinhold, Tarzana, CA (US); Kea-Tiong Tang, Hsinchu (TW); Sumit Yadav, Lake Forest, CA (US); Chunhong Zhou, Encinitas, CA (US); David Daomin Zhou, Valencia, CA (US); Pishoy Maksy, Newport Beach, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

(21) Appl. No.: 15/886,522

(22) Filed: Feb. 1, 2018

(65) Prior Publication Data
US 2018/0169413 A1  Jun. 21, 2018

Related U.S. Application Data

(62) Division of application No. 11/413,771, filed on Apr. 28, 2006, now Pat. No. 9,913,985.

(51) Int. Cl.
| | | |
|---|---|---|
| A61N 1/36 | (2006.01) | |
| A61N 1/05 | (2006.01) | |
| A61N 1/08 | (2006.01) | |

(52) U.S. Cl.
CPC ....... *A61N 1/36046* (2013.01); *A61N 1/0543* (2013.01); *A61N 1/36142* (2013.01); *A61N 1/36185* (2013.01); *A61N 1/0551* (2013.01); *A61N 1/08* (2013.01)

(58) Field of Classification Search
CPC ............ A61N 1/36046; A61N 1/36142; A61N 1/36185; A61N 1/0543; A61N 1/08; A61N 1/0551
See application file for complete search history.

(56) References Cited

U.S. PATENT DOCUMENTS

| | | | |
|---|---|---|---|
| 5,003,975 A | 4/1991 | Hafelfinger et al. | |
| 5,109,844 A | 5/1992 | de Juan, Jr. et al. | |
| 5,755,744 A * | 5/1998 | Shaw | A61N 1/08 607/45 |
| 5,935,155 A | 8/1999 | Humayan et al. | |

(Continued)

*Primary Examiner* — Catherine M Voorhees
(74) *Attorney, Agent, or Firm* — Scott Dunbar

(57) ABSTRACT

In electrically stimulating neural tissue it is important to prevent over stimulation and unbalanced stimulation which would cause damage to the neural tissue, the electrode, or both. It is critical that neural tissue is not subjected to any direct current or alternating current above a safe threshold. Further, it is important to identify defective electrodes as continued use may result in neural damage and further electrode damage. The present invention presents system and stimulator control mechanisms to prevent damage to neural tissue.

9 Claims, 7 Drawing Sheets

(56) References Cited

U.S. PATENT DOCUMENTS

| | | |
|---|---|---|
| 5,944,734 A | 8/1999 | Greenberg et al. |
| 6,391,024 B1 | 5/2002 | Sun et al. |
| 6,400,989 B1 | 6/2002 | Eckmiller |
| 6,458,157 B1 | 10/2002 | Suaning |
| 6,718,209 B2 | 4/2004 | Williamson et al. |
| 6,974,533 B2 | 12/2005 | Zhou |
| 2002/0072770 A1* | 6/2002 | Pless ................. A61N 1/36064 607/2 |
| 2002/0177882 A1 | 11/2002 | DiLorenzo |
| 2003/0236558 A1* | 12/2003 | Whitehurst .......... A61N 1/0556 607/45 |
| 2004/0064161 A1 | 4/2004 | Gunderson et al. |
| 2005/0222624 A1 | 10/2005 | Greenberg et al. |
| 2006/0129207 A1* | 6/2006 | Fried ................. A61N 1/36046 607/54 |

\* cited by examiner

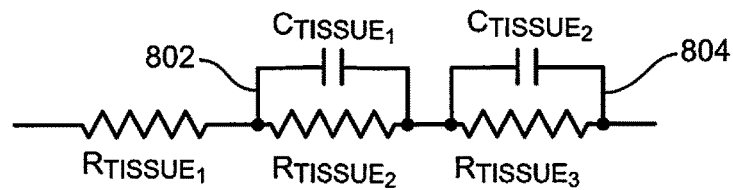
*Fig. 8A*
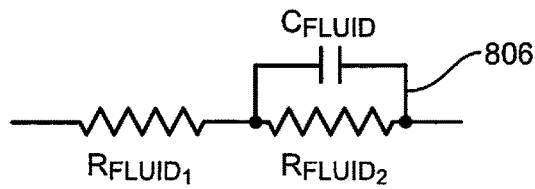
*Fig. 8B*
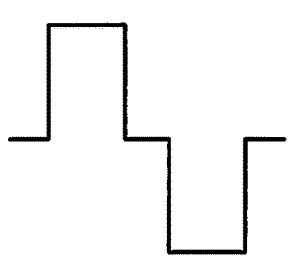 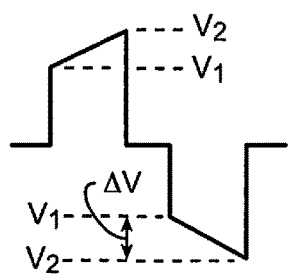 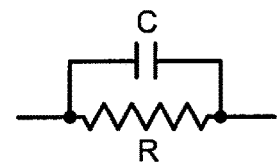
*Fig. 9A*   *Fig. 9B*   *Fig. 9C*
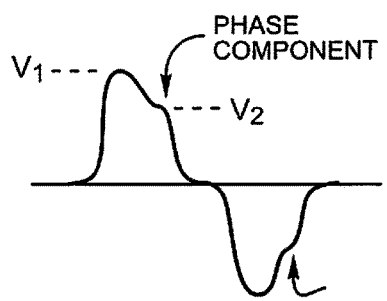 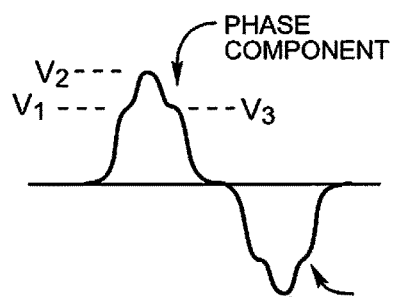
*Fig. 9D*   *Fig. 9E*

METHOD AND APPARATUS TO PROVIDE SAFETY CHECKS FOR NEURAL STIMULATION

CROSS REFERENCE TO RELATED APPLICATIONS

The present application is a divisional application of U.S. patent application Ser. No. 11/413,771, filed Apr. 28, 2006, for Method and Apparatus to Provide Safety Checks for Neural Stimulation.

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to neural stimulation and more specifically to an improved method of providing safety checks to prevent neural damage.

BACKGROUND OF THE INVENTION

In 1755 LeRoy passed the discharge of a Leyden jar through the orbit of a man who was blind from cataracts and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparatuses to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations, including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretial). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated a cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 µA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails," having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

SUMMARY OF THE INVENTION

In electrically stimulating neural tissue, it is important to prevent over stimulation and unbalanced stimulation which would cause damage to the neural tissue, the electrode, or both. It is critical that neural tissue is not subjected to any direct current or alternating current above a safe threshold. Further, it is important to identify defective electrodes, as continued use may result in neural damage, and further electrode damage. The present invention presents system and stimulator control mechanisms to prevent damage to neural tissue.

BRIEF DESCRIPTION OF THE DRAWINGS

FIGS. 8a and 8b are schematic representations of the electrode tissue interface.

FIGS. 9a-9e are wave forms illustrating the effects of altering the electrode tissue interface.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
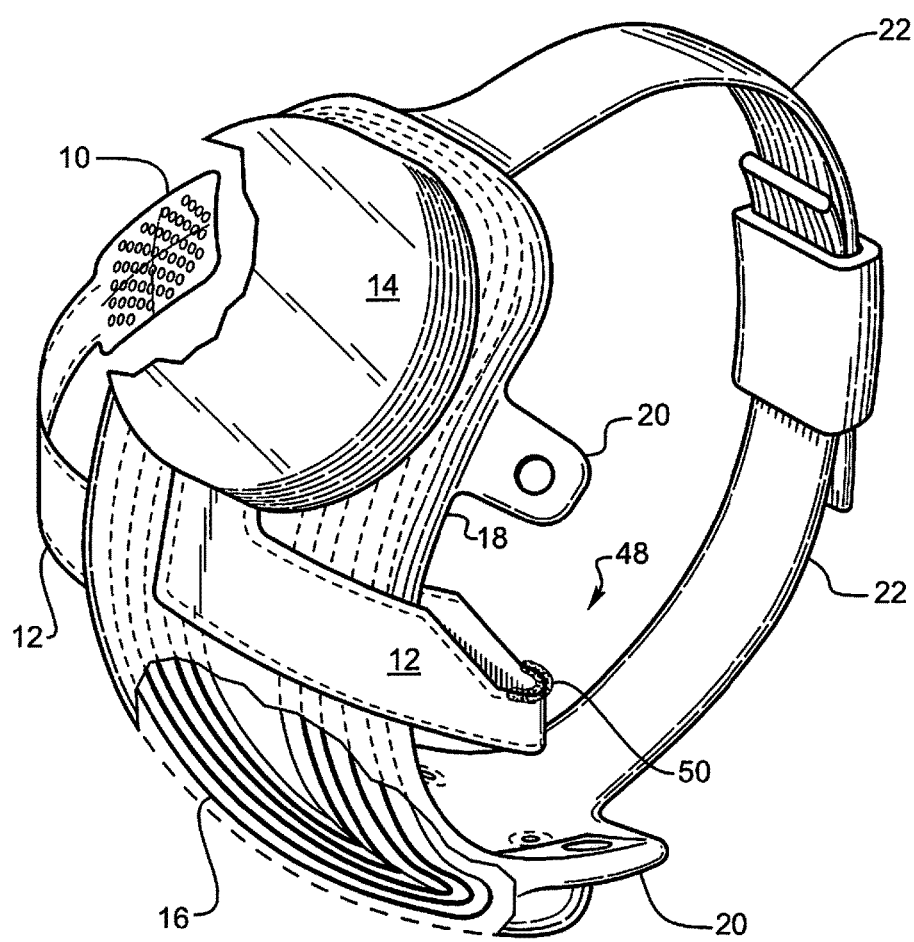
FIG. 1 is a perspective view of the implanted portion of the preferred retinal prosthesis.

FIG. 1 shows a perspective view of the implanted portion of the preferred retinal prosthesis. While the invention has broad applicability to neural stimulation, the preferred embodiment is a retinal prosthesis. A flexible circuit includes a flexible circuit electrode array 10 which is mounted by a retinal tack (not shown), or similar means, to the epiretinal surface. The flexible circuit electrode array 10 is electrically coupled by a flexible circuit cable 12, which pierces the sclera and is electrically coupled to an electronics package 14, external to the sclera.

The electronics package 14 is electrically coupled to a secondary inductive coil 16. Preferably, the secondary inductive coil 16 is made from wound wire. Alternatively, the secondary inductive coil 16 may be made from a flexible circuit polymer sandwich with wire traces deposited between layers of flexible circuit polymer. The electronics package 14 and secondary inductive coil 16 are held together by a molded body 18. The molded body 18 may also include suture tabs 20. The molded body 18 narrows to form a strap 22 which surrounds the sclera and holds the molded body 18, the secondary inductive coil 16, and the electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped coil.

The preferred prosthesis includes an external portion (not shown) which includes a camera, video processing circuitry and an external coil for sending power and stimulation data to the implanted portion.

Figure 2:
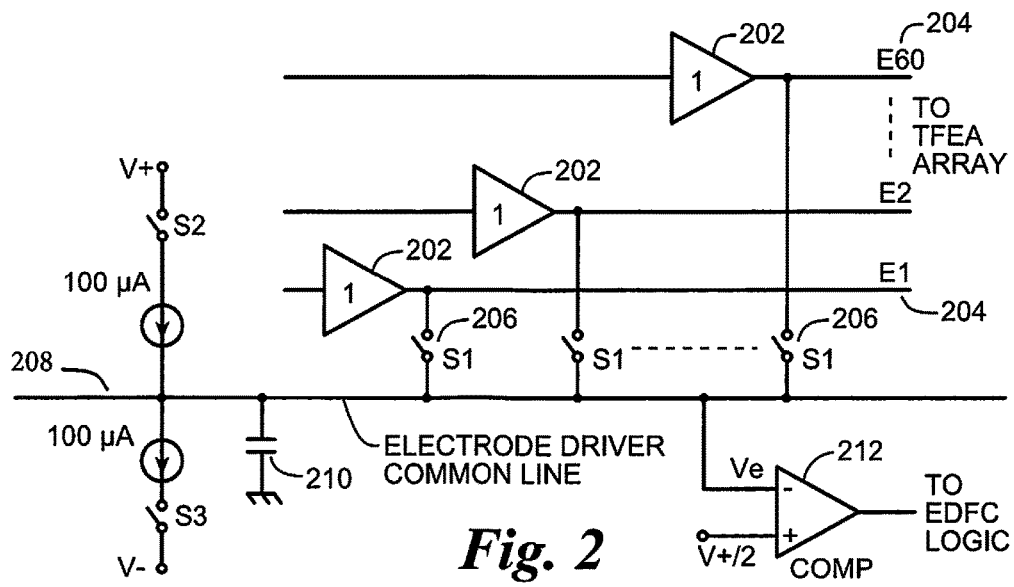
FIG. 2 is a schematic of a circuit for detecting excessive direct current flow.
Figure 3:
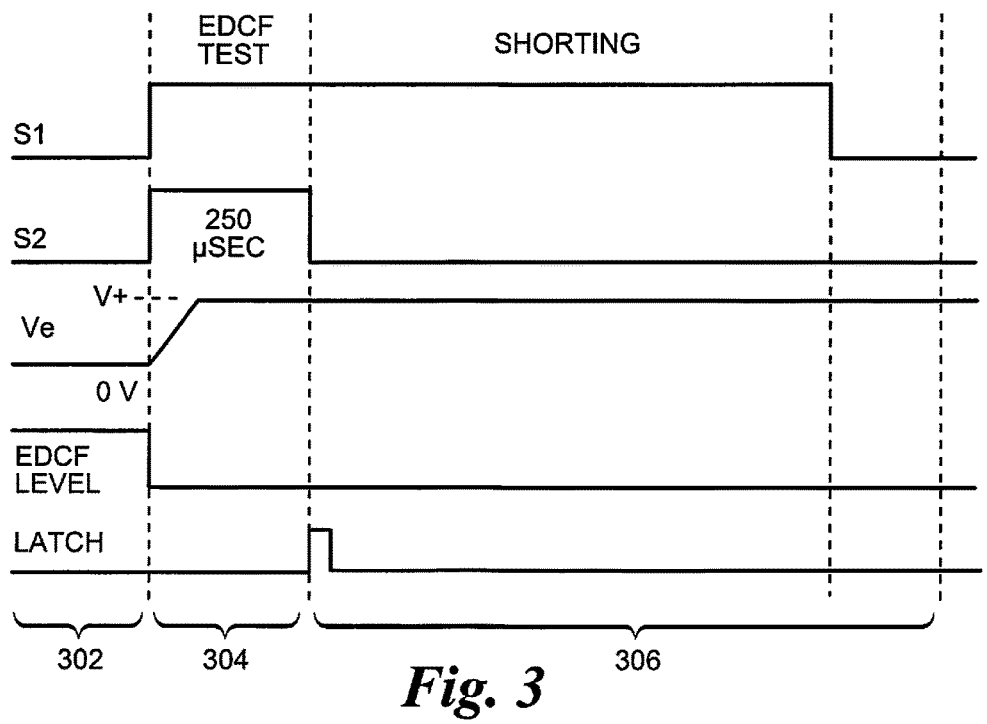
FIG. 3 is a timing diagram of detecting excessive direct current flow.

The electronics package 14 includes an integrated circuit for controlling stimulation. The integrated circuit includes an excessive direct current flow (EDCF) detection circuit as shown in FIG. 2. In the implant or saline environment, a certain amount of continuous DC current passing through an electrode array will cause bubbling which may result in damage to neural tissue. The EDCF circuit detects harmful DC leakage levels and transmits this information through the inductive coil 16 to the external electronics. The integrated circuit in electronics package 14 includes a plurality of drivers 202, one for each stimulation electrode 204, in the electrode array 10. When the external electronics initiates an EDCF cycle, switches 206 connect each driver 202 to an electrode driver common line 208. Any DC leakage current from the drivers 202 will flow through the electrode driver common line 208. In a fault condition, a leakage could flow through the driver output to either of the power rails, therefore, both sides are tested in alternate stimulation frames. In a particular test, one of the two currents of threshold values is turned on to charge the node capacitor 210 of the common line. There is no physical node capacitor 210. The node capacitor 210 is inherent capacitance in the integrated circuit. If there is a leakage path larger than the threshold value in the opposite direction, the potential of the common line is held toward the leakage side. A comparator 212 detects the potential against a predetermined middle potential. The output of the comparator 212 is captured after a predetermined interval, preferably 250 µs, which is then interpreted by EDCF control logic. The integrated circuit further includes power switches such that, in case there is an EDCF error (i.e. the DC leakage level exceeds the set threshold, preferably 100 µA), the external electronics will cut off power to the electrode driver circuits and block the leakage source. FIG. 3 shows the typical timing of the ECDF system. A stimulation cycle 302 is followed by the ECDF cycle 304, followed by a shorting cycle 306. Shorting will bleed off any trace amounts of DC build up.

Electrode bubbling occurs when the voltage across the double layer of the electrode-tissue interface exceeds a threshold voltage window over a certain time duration during the stimulation cycles. This threshold voltage window is found to be around ±1.5V for a flexible circuit electrode array 10.

Figure 4:
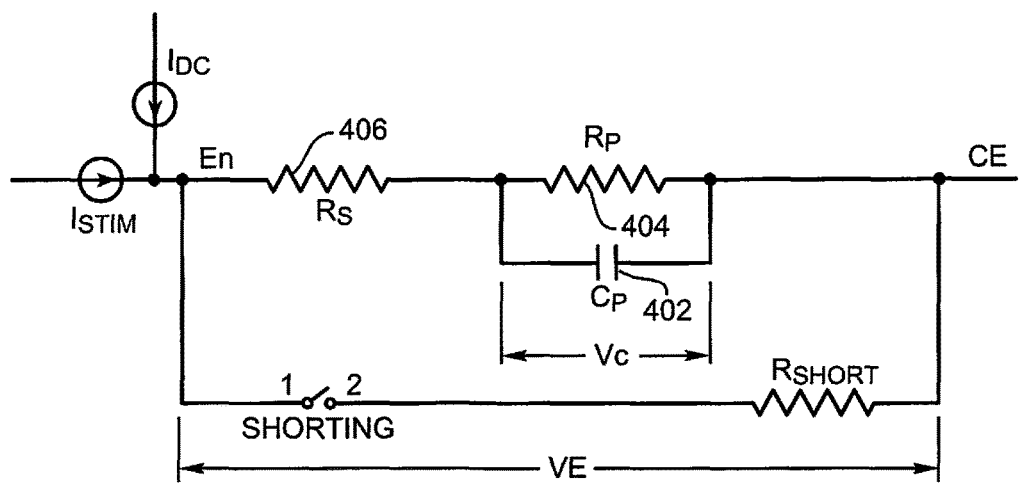
FIG. 4 is a schematic of a circuit for detecting build up of low level direct current flow.

Based on the simplified electrical model of the electrode shown in FIG. 4, we can see that the charge buildup on the electrode is reflected with the voltage across the double layer capacitor Cp 402. During normal stimulation with balanced biphasic current pulses, the maximum voltage across the cap occurs at the end of the first current pulse of amplitude I:

$$V_{Cmax} = IR_p(1 - e^{-Tx/\tau_p}) + V_C(0)e^{-Tx/\tau_p} \approx V_C(0) + \frac{Q_x}{C} \text{ for}$$

$$t \ll 1, \text{ and } R_p \gg 1)$$

Where Vc(0) is the initial voltage caused by the residue charge left on the capacitor at the end of shorting, $\tau_p=R_pC_p$ (404, 402) is the time constant of the leaky double layer, Tx is the pulse duration, and Qx is the total charge of the first stimulation phase flown through the electrode.

Figure 5:
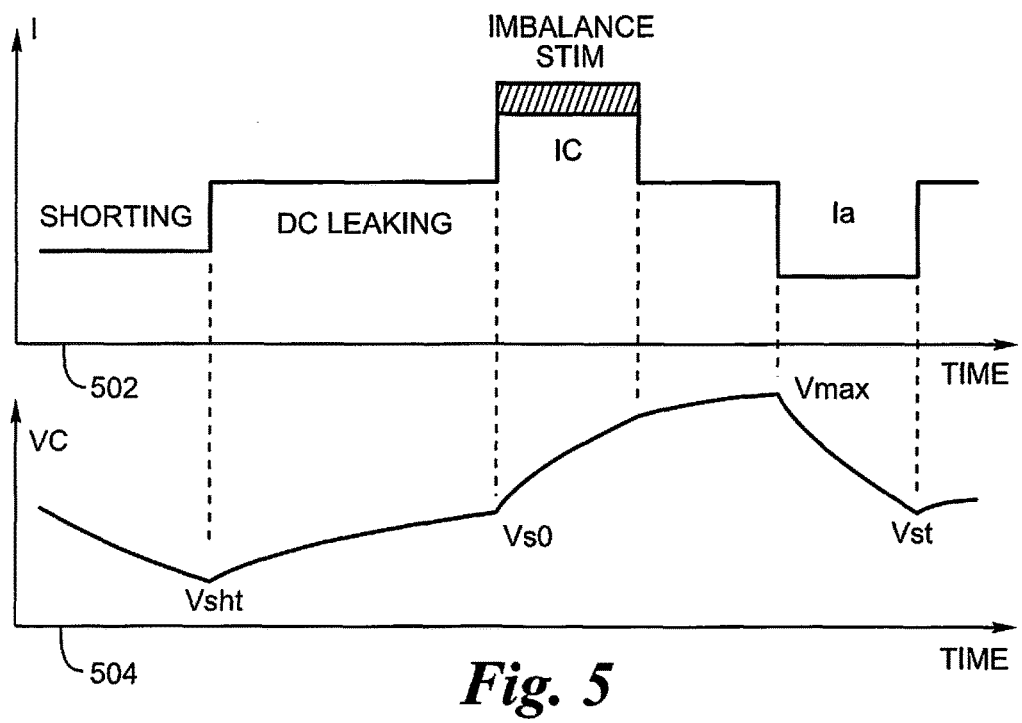
FIG. 5 is a timing diagram of detecting build up of low level direct current flow.

When a DC leakage is present, the charge is built up even when the system is not stimulating. The worst case is when the DC leakage is in the same polarity as the first phase stimulation current. If the leakage current is small compared to the stimulation current, which may be the case, the worst case voltage build up on the electrode occurs when the stimulating pulse happens just before the shorting starts. In this case, the maximum electrode voltage is at the start of the second current pulse, which is illustrated in FIG. 5. The maximum voltage is:

$$V_{Cmax}=I_LR_p+I_SR_pe^{-Tx/\tau_p}(1-e^{-Tx/\tau_p})+(V_C(0)-I_LR_p)e^{-(T-T_{P7}-Tx)/\tau_p}$$

Where $I_L$ is the leakage current, $I_S$ is the stimulation current, $T_{P7}$ is P7 profile duration that includes a shorting duration of $T_{SH}$=1.4 ms and 0.3 ms for the EDCF check, and T is the stimulation cycle.

A possible electrode voltage map is show in FIG. 5, showing a stimulation cycle in the presence of DC leakage that is smaller than the stimulation current. The upper graph 502 is the total current flowing through the electrode, and the lower graph 504 is the voltage on the double layer capacitor.

The measured parameters $C_p$ and $R_p$ of the electrodes are preferably 0.25-0.3 μF and 70-80 K'Ω; but 0.25 μF and 80 K"Ω to handle the worst case condition, which may result in $\tau_p$=20 ms. The shorting time is fixed at 1.4 ms in the preferred embodiment. The stimulation pulse duration Tx may also vary, but the smallest duration is confined by the implant compliance limit and will make the electrode less tolerant to leakage. From a 15 KΩ electrode impedance assumption, this will allow a 0.275 ms duration at a current of 400 μA (0.35mC/cm² maximum charge density). The maximum allowed imbalance of 5% should also be put in the equation. Therefore, in worst case condition, we have:

$$\tau_p=20\text{ ms, } Tx=0.275\text{ ms, } I_S=400\text{ μA, } T_{P7}=1.4\text{ ms,}$$
$$T=8.3\text{ ms}$$

From which we get:

$$V_{C\,max}=0.73V_C(0)+21.7I_L\text{ (mA)}+0.43\text{(V)} \quad (3)$$

This voltage should be kept below 1.5V. For a margin of safety, we set the maximum allowed electrode voltage across the double layer to be $V_{Cmax}$=1.0V.

The steady state value of the residue voltage on the capacitor depends on the shorting duration. It can be estimated as:

$$V_C(0)=V_{SH}(0)e^{-TSH/\tau_S} \quad (4)$$

where $\tau_S$ is shorting time constant, and $V_{SH}(0)$ is the voltage at the end of the cycle, just before shorting is turned on. In our worst case condition, we have:

$$V_{SH}(0)=V_{C\,max}\,e^{-Tx/\tau_p}-(I_S-I_L)R_p(1-e^{-Tx/\tau_p})=0.72$$
$$V_C(0)+22.5I_L-0.06$$

Where $\tau_S=R_{IR}C_P$=15K×0.25 μF=3.75 ms.

Therefore, with $T_{SH}$=1.4 ms, we have from (4) and (5):

$$0.73V_C(0)-22.5I_L+0.06=0 \quad (6)$$

From (3) and (6), we can calculate the maximum allowed as $$I_{Lmax}=12\text{ μA} \quad (7)$$

This maximum allowable leakage current for an individual electrode to ensure that it does not cause electrode bubbling is lower than the EDCF detection circuit (described in reference to FIGS. 2 and 3) threshold current which addresses the total leakage current of all channels. Therefore, a test is needed to detect if the leakage level of an individual channel passes the maximum allowed leakage value $I_{Lmax}$ estimated.

The electrode potentials take some time to stabilize because of the time needed to reach the balance between the charge released by shorting and the build up by charge imbalance or leakage. The above analysis on electrode voltages only addresses the steady state condition. Because a DC leakage is considered persistent current flow with or without the presence of stimulation, a simple method is used to measure the electrode voltage caused by the leakage current in quiescent condition in which all stimulation is turned off. This way the disturbance on the electrode voltage caused by the stimulation currents is avoided. On the other hand, the electrode voltage caused by the leakage current $I_L$ (if existent) is still a function of the shorting duration. When we use the same shorting strategy as the normal condition with EDCF turned off, i.e., $T_{SH}=T_{P7}$=1.7 ms, the steady state voltages on the electrode double layer are estimated:

$$V_{SH-}=V_{SH+}e^{-(T-T_{P7})/\tau_p}+I_LR_p(1-e^{-(T-T_{P7})/\tau_p})$$
$$\approx 0.718V_{SH+}+22.5I_L \quad (8)$$

$$V_{SH+}=V_{SH-}e^{-TSH/\tau_S}\approx 0.635V_{SH-} \quad (9)$$

Which give us:

$$V_{SH-}=0.50\text{V}; V_{SH+}=0.32\text{V}$$

Where $V_{SH-}$ and $V_{SH+}$ are the voltages immediately before and after the P7 pulse. Either $V_{SH-}$ or $V_{SH+}$ can be used as the individual electrode leakage threshold; however, $V_{SH-}$ is preferred because of its higher value for better accuracy of the measurement. The voltage driver output $V_{DO}$ is the sum of the I-R drop caused by the real part of the electrode-tissue impedance $R_S$ 406 and the electrode voltage on the double layer capacitor $V_C$ discussed above. The I-R drop can be calculated as $I_LR_{ir}$, where $R_{ir}$ is the electrode impedance.

From (7), the I-R drop caused by the allowed maximum DC leakage current is $I_{Lmax}R\approx$0.12-0.56V constant for electrode impedances ranging 10-40 KΩ. However, when the electrode is lifted from the retina, the impedance could be lowered to as small as 3 KΩ. For a relatively accurate estimation of the leakage current using the $V_{DO}$ measurement, the I-R drop should be subtracted from the $V_{DO}$ result using the pre-measured electrode impedance values. For simplicity, it may be preferable to ignore the I-R drop effects in this leakage detection protocol and directly use the $V_{DO}$ data as the electrode voltage $V_C$. Ignoring the I-R drop will yield a 20-50% inaccuracy of the leakage value estimation that will result in a more conservative monitoring. This will not compromise the safety but will simplify the measurement.

In our electrode impedance measurement protocol, an electrode with impedance 65 KΩ or higher is labeled as an open electrode. Stimulation to an open electrode is turned off. However, it must be noted that an electrode with impedance higher than 65KΩ could still bubble because of DC leakage. Assume that the maximum allowed leakage is still 12 μA and the compliance limit for the leakage current is 7.0V, and we can calculate with the same method used above that an electrode with impedance value as high as 450 KΩ will reach electrode bubbling status. However, the measured voltage is limited to about 4V on the anodic side, which will limit the detectable threshold leakage to electrodes with impedance up to 230KΩ. For example, if the measured electrode impedance is 200KΩ, then a measured $V_{DO}$ of 3.4V or more can be considered a bubbling status. In either case, the electrode impedance measurement should be able to discriminate between a high impedance electrode and an open electrode.

The following method is suggested to label an electrode as a high impedance (HI) electrode: After the regular impedance measurement routine, all "open" electrodes (if any) are measured again using 8.1 μA/1 ms current pulses with the $V_{DO}$ sampling point set at 0.9 ms after the pulse start. An electrode with measured impedance 500KΩ or less ($V_{DO}<\pm4V$) shall be tagged as HI electrode, while higher impedance electrodes are tagged as open.

For HI impedance electrodes, the build up voltage on the electrode capacitor is solely from DC leakage because they are not stimulated. Therefore, the maximum allowed electrode voltage is simply $V_{SH-}=1V$, plus the I-R component when using $V_{DO}$ measurement. Therefore, the threshold for an HI electrode should be $V_{DO}$ (measured at $V_{SH-}$):

$$VDO|_{V_{SH-}} <= I_{Lmax}R+1 \approx 0.012R \text{ (K}\Omega\text{)}+1 \tag{10}$$

Considering the limited ADC range in the anodic direction, it may be preferable to check all HI electrodes with impedance 200 KΩ or higher against the threshold voltage of 200 KΩ, which is 3.4V.
For open electrodes, this checking procedure can be omitted.

Figure 6:
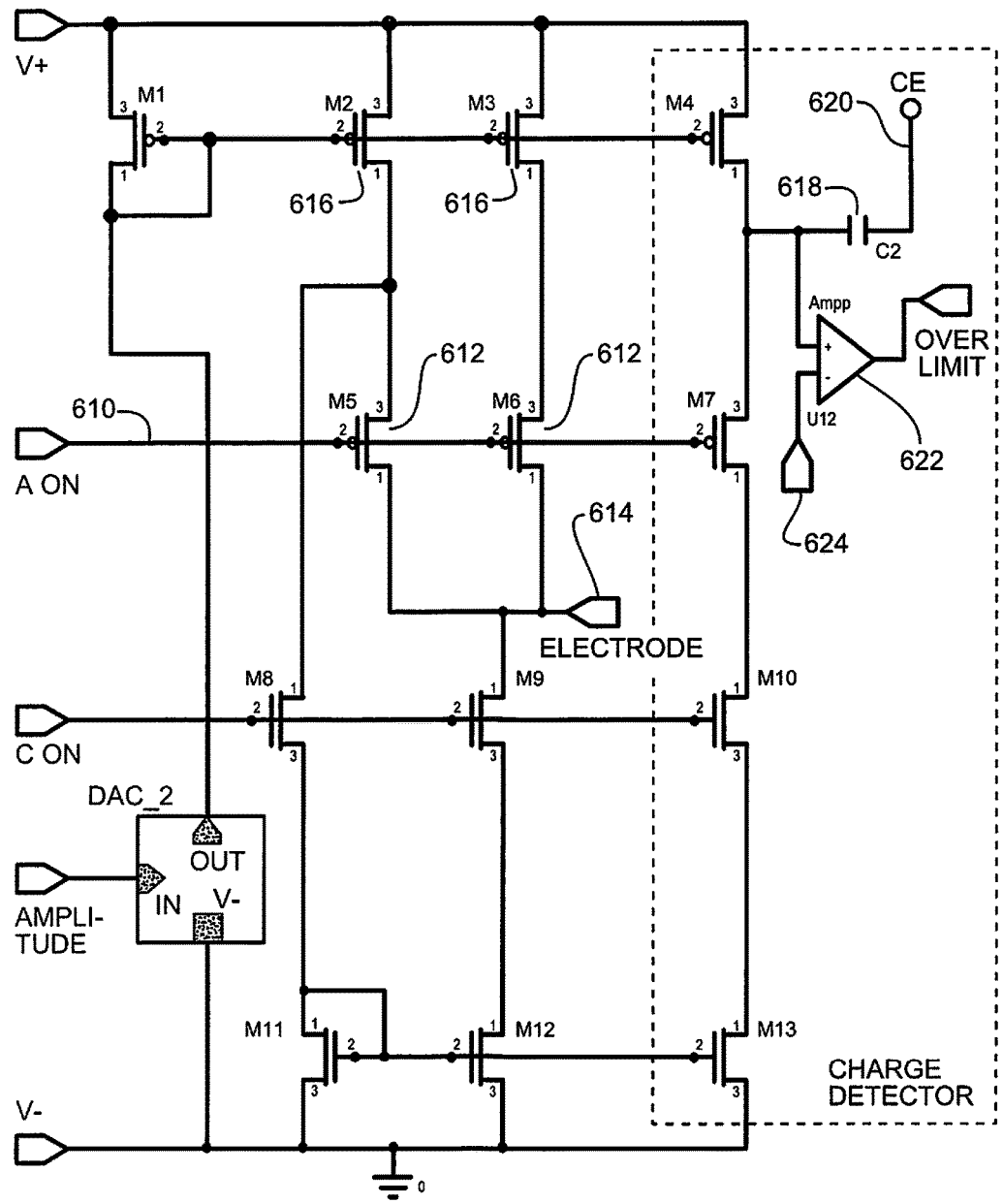
FIG. 6 is a schematic of a circuit to detect exceeding a maximum charge per phase.

Referring to FIG. 6, the problem of exceeding maximum charge per phase (MCPP) can be solved with two different methods. In one case, the cathodic and anodic pulse amplitude of each electrode is multiplied by the phase duration, and the result is checked against a predetermined MCPP value. If the value is exceeded, the amplitude value is clipped to achieve the limit. This first method is accurate for square waves, but becomes less accurate as the stimulation wave form becomes arbitrary. In another method, a discrete integral is taken in the time representation of the pulse to calculate the charge. If the integral at any point of time exceeds the absolute MCPP value (positive or negative), the amplitude value is either clipped to achieve the limit or zeroed out. Another method that could be used is by an active current monitor on the stimulator device, which limits the current to a particular MCPP. For all these methods, the implementation will be stimulator setting dependant (e.g. Frequency setting) so that the safety checks will adapt to limit the charge to the MCPP in any case.

The circuit shown in FIG. 6 performs an integration of the waveform through capacitance charge. The stimulation signal 610 is amplified in transistors 612 to drive the stimulating electrode 614. Simultaneously, the stimulation signal 610 is amplified in transistors 616 to create a much smaller, but proportional charge signal. Capacitor 618, between the charge signal output and the common electrode 620 is charged by the charge signal. Comparator 622 compares the charge on capacitor 618 with a predetermined maximum charge 624 and generates an over limit signal when the charge on capacitor 618 is over the predetermined maximum charge.

Another way to limit current density is to provide a compromise between the monopolar mode and bipolar mode of stimulation. The method includes setting up stimulation wave forms as in bipolar stimulation mode without disconnecting the common electrode (ground). A portion of the current will flow between the electrodes, and a portion of the current will flow between the electrodes and ground. The ratio of current flow will depend on electrode impedance. This hybrid bipolar mode of stimulation could possibly result in lower thresholds than can be obtained from a true bipolar mode of stimulation, and also has the advantage of greater selectivity than can be obtained from a monopolar mode of stimulation. To set up a safe hybrid bipolar stimulation wave form, the two electrodes concerned should have balanced biphasic currents going in opposite phases at exactly the same times, with the common electrode connected. If the pulse waveforms are balanced by themselves on each electrode but overlap non-contiguously in opposite phases with other electrodes in the array, a resultant unbalanced current could flow through the tissue eventually causing neural tissue damage. A safety check method could be implemented in the external electronics to prevent such unbalanced multipolar waveforms to be sent to the stimulator. The above phenomenon and safety check method is also applicable to multipolar forms of stimulation (i.e. in addition to bipolar).

It is also important to limit the maximum stimulation across all electrodes in an electrode array. While each electrode is individually stimulating at a safe level, there can still be neural damage, or even in some cases, pain, if all electrodes are stimulating at or near their individual maximum level. Hence, it is important to track and limit the sum total stimulation from all electrodes. This is a simple calculation that can be done with software in the external electronics. For each stimulation cycle, all stimulation values are summed and compared with a predetermined maximum. If the sum exceeds the predetermined maximum, the stimulation is reduced, either proportionally across all electrodes, or by limiting electrodes set to higher stimulation levels.

Broken electrode detection can be achieved with a method of monitoring impedance of the electrodes (over time (delta I), as well as comparing impedances of electrodes to its neighboring electrodes in the media, and incorporation of physiological data as observed from physicians). When a broken electrode is found in the system, the stimulator device is commanded to halt stimulation on that broken electrode—with the history of electrode damage logged and persistent in the stimulator controller. Visually, the electrode health is represented through a color/topographical map of the electrode array on a computer system. Optimally, a movie-like data playback of the impedances can be provided. Electrode damage can also consist of shorting between electrodes (as opposed to 'broken') which will also be detected through impedance monitoring.

Charge imbalance can be reduced by implementing a 1.4 ms shorting pulse prior to any stimulation on every stimulation frame of the stimulator. Additionally, the stimulator controller can adjust (and check) the anodic and cathodic current level, using amplitude parameter tables determined from the manufacturing tests of the stimulator, to achieve the best balance. The stimulator controller also checks that there exist no overlapping anodic/cathodic profiles that could cause a charge imbalance at the tissue. Another method of reducing charge imbalance on an electrode is by having the stimulator controller auto-balancing the pulse. Two ways of achieving this are by appending a square pulse after the pulse to compensate for the imbalance or by appending an inverted pulse to compensate. Check against DC flow in tissue from the electrodes is achieved through a combination of the ASIC test, the shorting function, and an initial individual electrode check implemented on startup (or periodically) by the stimulator controller. The issue of implant overheating is handled in multiple ways. Power is controlled on the retinal prosthesis through a feedback loop fed by implant back telemetry. Currently, this is achieved by inferring the implant heat through the current in the shunt regulators of the implant device. Additionally, if a thermistor is placed in the implant device, then the heat can be measured and returned to the controller through the back telemetry link.

Additionally, the instantaneous current output on the stimulator device is limited to a constant value by the controller. This ensures that no amount of instantaneous current is allowed that might expect the stimulator to reset due to lack of power. This instantaneous current limit could also be variable (instead of constant) with appropriate back telemetry and controller design. For system operational modes that do not allow heat control via the shunt current values, the controller performs a check that ensures the implant shunt current level can be set to a safe value immediately prior to the operational mode which doesn't provide shunt current information in the back telemetry. Also, the stimulator controller verifies the voltage setting with an ADC circuit upon any change of voltage to the RF power circuitry.

Figure 7A:
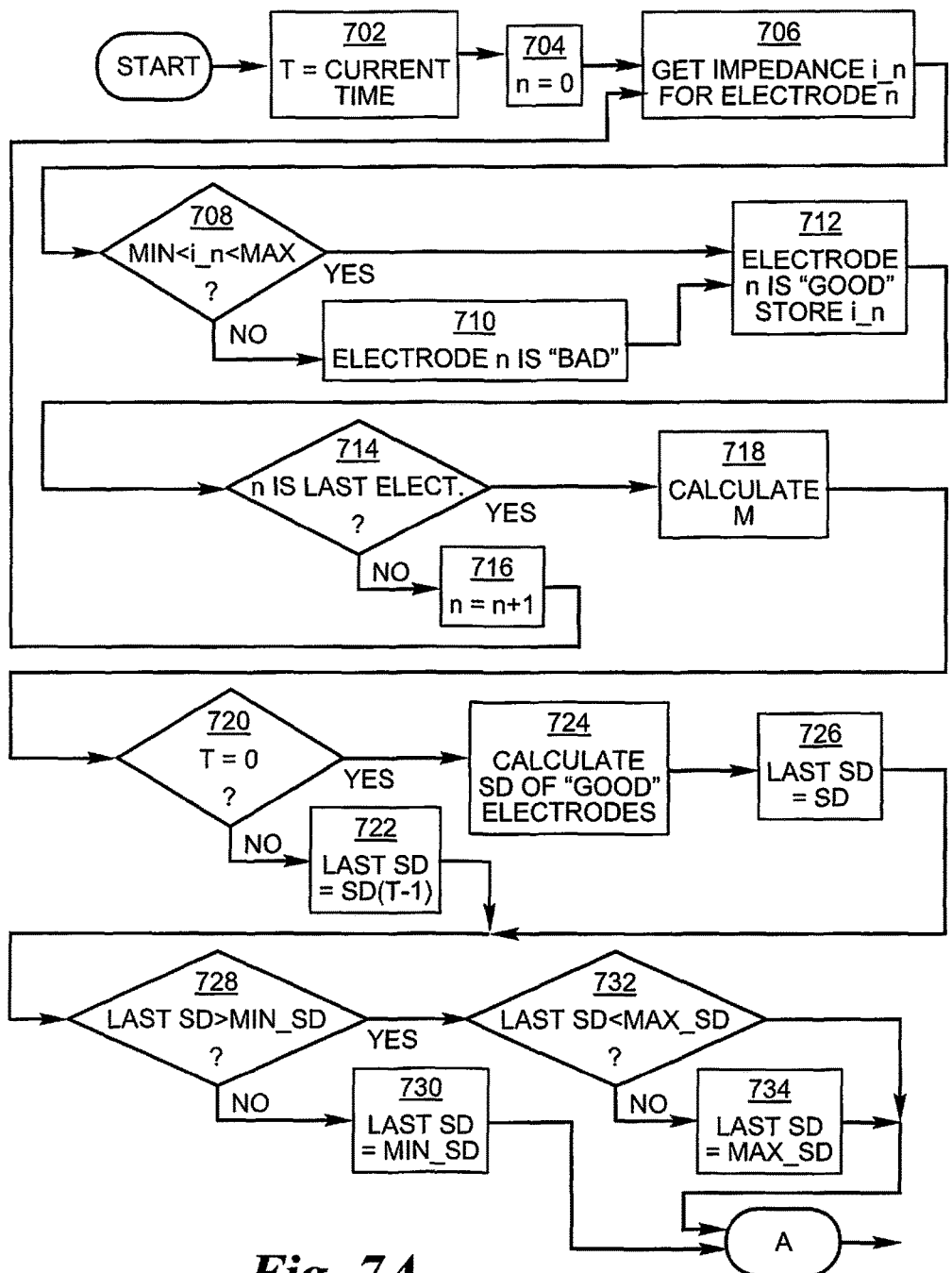
FIGS. 7a and 7b are flowcharts depicting a method for identifying defective electrodes.

Referring to FIG. 7a, the electrode failure detection system includes a table of electrode impedance value that is N, the number of electrodes, by T, the time history stored, and a table of electrode state values with three states, good, questionable, and bad. Each test begins by loading a time value 702 to identify the test. The electrode counter is set to zero 704, and the first electrode is tested 706. The system determines if the electrode impedance is within hard limits 708. These limits are the same for all electrodes. This can be used to catch the most obvious failures. As an illustration, the impedance value returned can range from 0Ω (complete short) to 65,535Ω (complete open), where the nominal value for a good electrode might be in the range of 10,000Ω to 20,000Ω. Here, a lower limit of 2,000Ω and an upper limit of 50,000Ω could be used, where any electrode falling outside these ranges would definitively be experiencing a failure and will be marked bad 710. If the electrode is within the hard limits, the electrode impedance is stored in the table 712. The process is repeated 714 incrementing the electrode counter 716 each time.

Once all electrodes have been tested, the system calculates and stores a median and standard deviation 718. If the test has been previously preformed 720, the impedance data is shifted to the next memory location 722. If not, it calculates the standard deviation of good electrodes 724, and shifts the standard deviation to the previous memory location 726. If the electrode values are close, a very low standard deviation may trigger too many electrodes marked as bad. Hence the standard deviation is compared with a preset minimum 728 and replaced with the minimum if the minimum is higher 722. If the electrode values are far apart, a very high standard deviation may not mark bad electrodes. Hence the standard deviation is compared with a preset maximum 730 and replaced with the maximum if the maximum is lower 732.

It has been observed that an electrode which fails (reading as high as 65 kΩ initially) may give subsequent impedance values which begin to fall, sometimes returning to a nominal, good value. This is apparently due to fluid leaking in the broken area and creating an alternative (and undesirable) conduction path. Thus, any one set of readings may not show all electrodes known obviously to be broken, and a history must be maintained. If an electrode ever exceeds the limits, it is considered permanently failed.

Note the history of the electrodes should not begin until the implantation of the array has stabilized. Impedance readings are very useful through the implantation process, but values may shift drastically, and false failures can impede the process.

It appears many failed electrodes never reach a high value, or reach it and return so quickly it may not be recorded. Thus, additional checks are required.

Figure 7B:
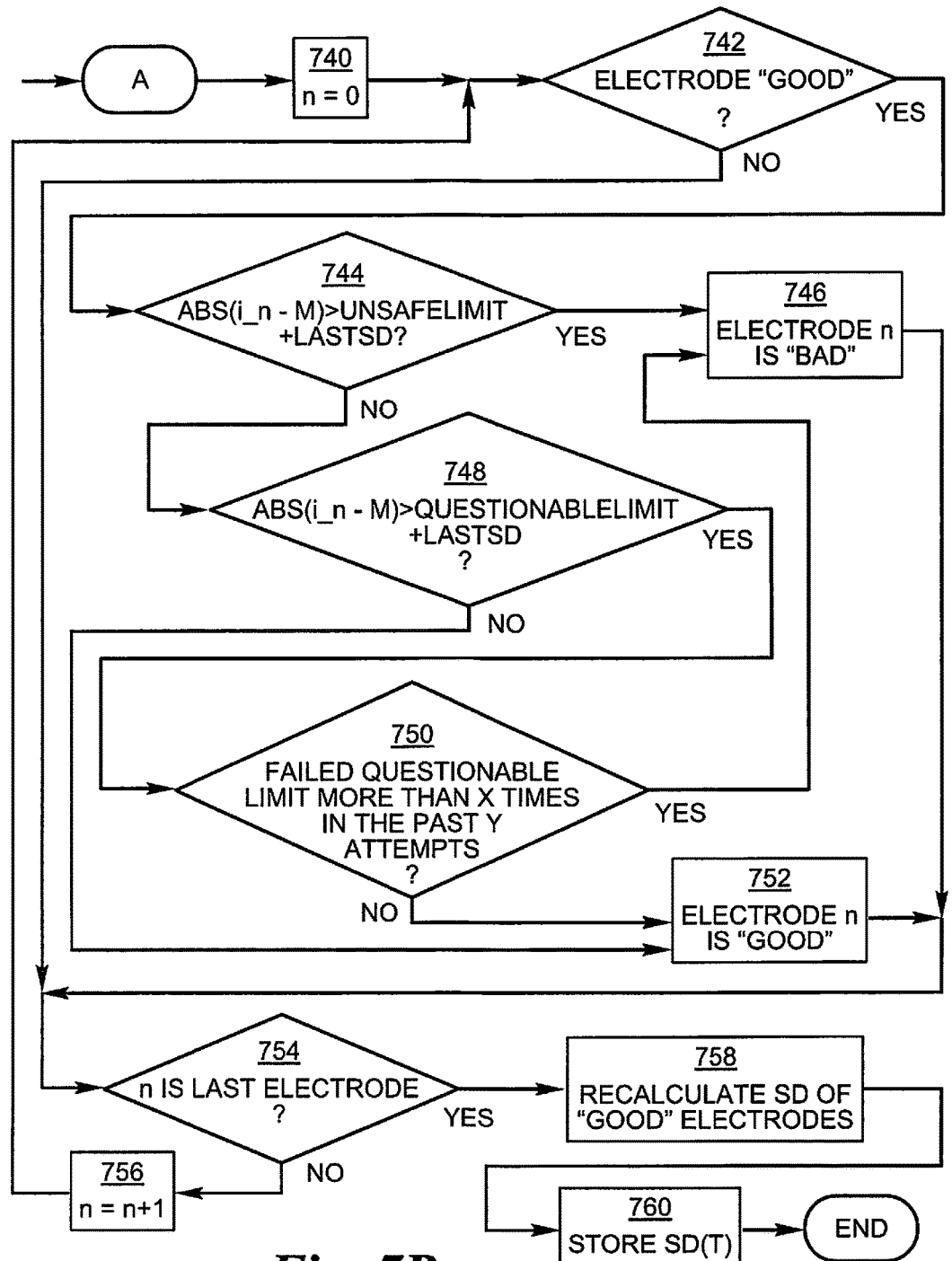

Referring to FIG. 7b, the electrode counter is again set to zero 740. If the electrode is already marked bad 742, it cannot be marked good again. For each electrode, if the absolute value of the electrode impedance minus the median is greater than an unsafe limit times the standard deviation 744, the electrode is marked as bad 746. In the preferred embodiment, the unsafe limit is four times the standard deviation. If the absolute value of the electrode impedance minus the median is greater than a questionable limit times the standard deviation 748, and the electrode has measured questionable a predetermined number of times previously 750, the electrode is marked as bad 746. In the preferred embodiment, the questionable limit is three times the standard deviation. The process is repeated until all electrodes have been checked 754, with the electrode counter incremented each time 756. Finally, the standard deviation is recalculated for the remaining good electrodes 758 and stored 760.

In the preferred embodiment, impedance is used to determine the electrode integrity at the interface of the neural stimulator and tissue, as well as the integrity of the electrode stimulation path through the implantable device. However, data obtained both in vitro and in vivo show that these impedance readings are time dependent, and any given temporal snapshot may show failed electrodes as having perfectly nominal values. Furthermore, potentially critical failures such as electrode movement or loss of tissue contact may not be quickly diagnosed using the current methods as the changes in impedance may not be large.

Capacitance measurement is a possible solution since electro-neural interfaces have distinct capacitive characteristics. Referring to FIG. 8a, an interface between an electrode and tissue is actually two interfaces, one from electrode to fluid 802 and a second from fluid to tissue 804 as shown in FIG. 8. However, when an electrode lifts off tissue, the resulting circuit resembles a single electrode fluid interface 806, as shown in FIG. 8b. When an electrode is making good tissue contact, it follows the tissue model shown in FIG. 8a, with an average value of 15 k-25 kΩ. When an electrode has completely lifted-off, it follows the fluid model shown in FIG. 8b. It is designated 'fluid' since the values & characteristics of an implanted array lifted up in fluid are the same as that in saline in the laboratory.

When an electrode begins to lift off, it begins making contact with the fluid, and thus has two parallel impedance paths. A simple impedance measurement will show only a slight drop at the beginning. However, the phase characteristics of the two paths are different, both in total capacitance value and total phase shift. Thus, the waveform should show the effect.

Referring to FIG. 9 for a simple model on how a capacitor would affect an AC square wave. Initially it may appear simple to measure $V_2$ and $V_1$ and establish $\Delta V$ as $V_2-V_1$ and thus a measure of capacitance, as $\Delta V$ would increase as the total capacitance in the circuit increases. However, as given in the schematic of a typical electrical model of the electrode-tissue interface, FIG. 8, the portion of electricity going through the capacitor is phase shifted by 90°. The resultant waveform does show a capacitive phase shift, but with rounded peaks potentially anywhere on the waveform, so $\Delta V$ would not be a measure of capacitance. A method is required that accounts for this phase shift which could reflect the total capacitance as well as changes in its characteristics.

The difference in capacitance between the various electrical paths which occurs in both healthy and failed electrodes will be manifested as a phase difference in the various waves that sums the resultant measured waveform. This difference can be computed for each stimulation phase, based on the area of the curve of the first derivative, subtracting the baseline waveform where no phase shift is present. Healthy electrodes appear to have distinctive measurable characteristics in both anodic and cathodic phases. These characteristics change significantly when an electrode is losing contact at the neural interface (array lift-off) or is degrading, and thus electrodes which show a significant difference in phase shift are likely experiencing the manifestation of a failure. This method could be used to detect array lift-off potentially before it would be detected by the associated impedance values currently in use.

Accordingly, what has been shown is an improved method of stimulating neural tissue for improved response to brightness. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

The invention claimed is:

1. A method of stimulating neural tissue comprising:
providing an implantable neural stimulator including a plurality of electrodes suitable to stimulate neural tissue, each electrode electrically connected to a driver;
measuring impedance of the interface between the electrode and the neural tissue, using driver output voltage;
stimulating the neural tissue according to a programmed device which receives input external from the programmed device;
measuring an after stimulation driver output voltage, wherein the after stimulation driver output voltage is the I-R drop across the interface between the electrode and the neural tissue; and
calculating leakage current using the impedance and after the stimulation driver output voltage.

2. The method according to claim 1, wherein the external input is video input from a video processor.

3. The method according to claim 1, wherein the step of stimulating neural tissue is stimulating visual neural tissue to form artificial vision.

4. The method according to claim 1, wherein said step of stimulating neural tissue according to external input includes receiving input from multiple sources.

5. The method according to claim 1, wherein the step of stimulating neural tissue is stimulating retinal tissue.

6. The method according to claim 1, wherein the step of stimulating neural tissue is stimulating with charged balanced cathodic and anodic pulses.

7. The method according to claim 6, further comprising shorting said electrodes to ground after said anodic pulses.

8. The method according to claim 1, further comprising disabling a driver related to an electrode within the plurality of electrodes when leakage current is detected on the electrode.

9. The method according to claim 1, further comprising transmitting an error signal when leakage current is detected.

* * * * *